(12) United States Patent
Eide et al.

(10) Patent No.: US 9,433,691 B2
(45) Date of Patent: Sep. 6, 2016

(54) ROOM CLEANING SYSTEM AND METHOD

(71) Applicant: AERUS LLC, Dallas, TX (US)

(72) Inventors: Andrew Eide, Rockwall, TX (US);
Joseph P. Urso, Dallas, TX (US); Carl C. Christoff, Dallas, TX (US);
Timothy Raymond Vadnais, Plano, TX (US); Chad Darris Recer, Frisco, TX (US)

(73) Assignee: AERUS LLC, Dallas, TX (US)

( * ) Notice: Subject to any disclaimer, the term of this patent is extended or adjusted under 35 U.S.C. 154(b) by 270 days.

(21) Appl. No.: 14/463,206

(22) Filed: Aug. 19, 2014

(65) Prior Publication Data
US 2015/0047373 A1    Feb. 19, 2015

Related U.S. Application Data

(60) Provisional application No. 61/867,451, filed on Aug. 19, 2013.

(51) Int. Cl.
| *A61L 2/18* | (2006.01) |
| *A61L 9/00* | (2006.01) |
| *A61L 2/00* | (2006.01) |
| *A47L 9/00* | (2006.01) |
| *A61L 9/20* | (2006.01) |

(52) U.S. Cl.
CPC .. *A61L 2/00* (2013.01); *A47L 9/00* (2013.01); *A61L 9/00* (2013.01); *A61L 9/205* (2013.01); *A61L 2/18* (2013.01); *A61L 2209/14* (2013.01)

(58) Field of Classification Search
CPC ................................. A61L 2/00; A61L 9/00
USPC ........................................................... 422/28
See application file for complete search history.

(56) References Cited

U.S. PATENT DOCUMENTS

| 5,186,759 A | 2/1993 | Yacobellis |
| 5,258,408 A | 11/1993 | Steltenkamp |
| 7,767,141 B2 | 8/2010 | Andersson |
| 7,820,101 B1 | 10/2010 | Esquivel, II |
| 2004/0171511 A1 | 9/2004 | Nagai et al. |
| 2006/0104858 A1 | 5/2006 | Potember et al. |
| 2006/0288495 A1 | 12/2006 | Sawalski et al. |
| 2007/0207135 A1 | 9/2007 | Kritzler et al. |

FOREIGN PATENT DOCUMENTS

WO    9636483    11/1996

OTHER PUBLICATIONS

Patent Cooperation Treaty: International Preliminary Report on Patentablility for Related Application PCT/US2014/60274; Jan. 14, 2015; 10 pages, Jan. 14, 2015.
PCT: International Search Report and Written Opinion of PCT/US2014/32383 (related application), Jan. 14, 2015, 10 pgs, Nov. 21, 1996.

*Primary Examiner* — Kevin Joyner
(74) *Attorney, Agent, or Firm* — Howison & Arnott, L.L.P.

(57) ABSTRACT

A multi-step process for cleaning, disinfecting and substantially eliminating allergens in a room is provided.

10 Claims, No Drawings

ROOM CLEANING SYSTEM AND METHOD

BACKGROUND

1. Field of the Invention

The present invention relates generally to systems and methods for cleaning a room or space such as methods to reduce the allergen exposure within the space or room.

2. Description of Related Art

Within the air purification industry, and in particular within the commercial air purification market, it can be difficult to insure that a space, such as a house, apartment, hotel room, motel room or similar enclosure is properly treated to provide an environment that is both clean and substantially free of allergens. This begins with the fact that many cleaning methods leave behind additional allergens and many allergen treatment processes to don sufficiently clean the space.

A need exists, therefore, for a process having the necessary steps to result in a clean and substantially allergen free environment in a space such as a house, apartment, hotel room, motel room or similar enclosures.

All references cited herein are incorporated by reference to the maximum extent allowable by law. To the extent a reference may not be fully incorporated herein, it is incorporated by reference for background purposes and indicative of the knowledge of one of ordinary skill in the art.

BRIEF SUMMARY OF THE INVENTION

The problems presented in providing a clean an substantially allergen free environment are solved by the systems and methods of the present invention. In accordance with one embodiment of the present invention, a multi-step process is provided for systemically cleaning, disinfecting and substantially removing all allergens from a room.

Other embodiments have been described wherein the tools used for this system are specified with more detail as to their desired characteristics.

Other objects, features, and advantages of the present invention will become apparent with reference to the detailed description that follow.

DETAILED DESCRIPTION

All references cited herein are incorporated by reference to the maximum extent allowable by law. To the extent a reference may not be fully incorporated herein, it is incorporated by reference for background purposes and indicative of the knowledge of one of ordinary skill in the art.

In the following detailed description of the preferred embodiments, reference is made to specific preferred embodiments in which the invention may be practiced. These embodiments are described in sufficient detail to enable those skilled in the art to practice the invention, and it is understood that other embodiments may be utilized and that logical mechanical and electrical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

The embodiments described below will be described in relation to a room which is not to be interpreted as limiting the process to s single room, but to a predetermined space, such as a hotel room which would include the restroom and closet space, or an apartment which would include all of the living space in the apartment, or a house which would include all of the living space within the house, or any occupied building or area such as but not limited to, commercial offices, daycare, elder care and retail. Therefore, any reference to a room shall not be intended to be limited to a single room unless the entirety of the enclosure is a single room.

The embodiments described below will be described as if a standard heating ventilation and air conditioning (HVAC) system were in installed in the room. Assumptions as to the layout and components of the HVAC system are not to be limiting. The embodiments will be effective on many different types of HVAC systems as will be apparent to one skilled in the art. For example, coils will refer to the coils that air from the room would pass over before returning to the room, whether the coils are being used as expansion coils as in a standard AC setup or as condensing coils as in a heat pump set up. The important aspect is that the air entering the room has just passed over the coils, not the function of the coils. Therefore, the use of the phrase HVAC system is intended to be inclusive of many styles of systems that provide heating, ventilation or air conditioning to the room.

The embodiments are most easily discussed in terms of standard Steps. There are 15 Steps to the standard embodiment as discussed below. Variations to the Steps and the order of performing the Steps will be discussed after the description of the Steps.

Step 1: Air Purifier Placement and Activation

An air purification system, such as the Guardian Air Purification system sold by Aerus LLC., is place within the room, but not within the HVAC system, and activated. The air purification system will remove airborne particulates and odors by means of ionization, carbon filtration, and HEPA filtration capable of removing particles as small as 0.1 µm. Air Purification system may also in technology to create oxidizers, other than Tree Tea Oil, to eliminate surface contaminants throughout the air purification system.

Step 2: Initial Vacuum

Using a HEPA vacuum cleaner, such as the Lux Guardian Platinum Canister Vacuum sold by Aerus LLC. or another Carpet & Rug Institute approved HEPA vacuum cleaner, all surfaces (hard and soft) of the room are vacuumed to remove dirt, dust, allergens and other types of organisms. Surfaces include carpeting, rugs, tile, wood, upholstered furnishings, drapes, desks, mattresses, pillows, chairs, etc.

Step 3: Clean & Treat the HVAC System

With the HVAC system turned off, the coils are vacuumed using HEPA vacuum cleaner to remove loose dirt and other contaminates built up on the coils. After vacuuming coils, a coil solution is applied by hand, not sprayed. The coil solution cleans the coils and disinfects in one step. No rinsing or separate disinfectant application is required after applying coil solution.

Step 4: HVAC Filter Replacement

The used HVAC filter is removed from the HVAC system and placed in an appropriate plastic bag for disposal. A new HVAC filter is installed.

Step 5: Hand Cleaning & Treating of HVAC Vents

All HVAC vents are removed and are vacuumed to remove surface dust and dirt and then cleaned by hand. After hand cleaning all vents are treated by hand with disinfectant, then reinstalled.

Step 6: Condensation Pan Treatment

Before closing up the HVAC system, a water activated enzyme tablet is placed in the HVAC condensation drip pan.

The enzyme tablet prevents the growth of mold and bacteria in the condensation water that accumulates in the pan during HVAC operation. No Tea Tree oil is used.

Step 7: Hard Surface Disinfection

Using either a hand operated air sprayer or micro cloth, all hard surface areas are treated with disinfectant to eliminate germs, bacteria and other contaminates that may be present. These would include desks, chairs, dressers, most other types of wooden furnishings, light switches, TV remote control, Telephone, thermostat, counter top, etc. No cleansing agent is applied, only disinfectant.

Step 8: Soft Surface Disinfection

Using a micro sprayer, such as the Healthy Home MicroSprayer sold by Aerus, LLC., a ULV fogger or similar device, all soft surface areas are treated with a dust mite and flea control product, such as Home Solutions dust mite & flea control sold by Aerus, LLC., and an allergen and odor neutralizing product, such as Home Solutions Allergen Relief with Odor Neutralizer sold by Aerus LLC. Soft surfaces would include drapes, upholstered furnishings, mattresses, pillows, etc. No cleansing agent is applied in this step.

Step 9: Carpet Treatment

Using a multi-functional cleaning device, such as the Lux Floor Pro sold by Aerus LLC or a similar device for applying shampoo to carpet, all carpeted surfaces in room are treated with a crystal drying shampoo, such as the Turbo Shampoo sold by Aerus LLC. The carpet is treated with a dust and mite control, allergen and odor control and a disinfectant to eliminate germs or bacteria, etc. in the carpet. This process is only done to the carpets and excludes all upholstery. This type of shampoo allows for deep cleaning without getting the carpeting too wet. Dry time for such shampoos is typically less than 1 hour, at which point it dries to a crystal.

Step 10: Hydroxyl Treatment

The room is treated with a hydroxyl process to ensure germs, bacteria, mold and other contaminates are eliminated from cracks and crevices or other hard to reach places. The hydroxyl process uses a photo catalytic system powered by UV light of different wavelengths to turn oxygen and humidity in the air into oxidizers that may be dispersed into the air, such as hydroxyls, vaporized hydrogen peroxide, and super oxides. Residual odors are eliminated as part of the hydroxyl process without producing substantial levels of ozone.

Step 11: Post Clean Vacuum

All carpeted areas of room are vacuumed with vacuum cleaner to remove the crystallized shampoo from the carpet. Allergens, dirt, dust mites, etc., which are trapped in the dried crystals of shampoo are removed by this process.

Step 12: Bedding

Mattresses and pillows are covered with protectors to prevent dust mite and allergens from getting onto the mattresses and pillows.

Step 13: Protectant Treatment

A protectant, such as the AllerGuard protectant sold by Aerus LLC., is applied to all surfaces using a ULV fogger or cloth to put a long lasting barrier that prevents the growth of bacteria, germs, mold and other types of contaminates. A ULV fogger is used to apply the protectant to soil surfaces such as drapes and upholstered furnishings. A cloth is used to apply the protectant to hard surfaces such as desks, chairs, telephone, remote control, light switches, door knobs, thermostat, etc. No cleansing agent is applied in this step, only the protectant.

Step 14: Permanent Air Purifier Placement

During the above steps it is expected that air purification system has been moved about the room to allow for the steps to occur as every surface must be accessed at some point. Air purification system is now turned off to allow for proper permanent placement. Air purification system is positioned within the room to provide ongoing efficacy and occupant comfort. Once in a permanent location, air purification system is turned back on.

Step 15: Vacuum

To aid in keeping flooring (soft or hard) free from contaminates, a vacuum cleaner, such as the Aerus Commercial Upright HEPA filter vacuum cleaner, is located within the room for use by occupant. This ensures each treated room is vacuumed each day with a product designed to remove contaminates brought in from the outside and between treatments.

Record Keeping

A Room Checklist & Release may be filled out as the process is being performed or shortly thereafter. A copy of the completed and signed Room Checklist & Release shall be maintained in electronic and/or hard copy. The Checklist & Release details the steps required for a given room and confirms that each step has been accomplished.

A copy of the completed Room Service Performance Checklist shall be maintained in electronic and/or hard copy.

It should be apparent from the foregoing that an invention having significant advantages has been provided. While the invention is shown in only a few of its forms, it is not just limited but is susceptible to various changes and modifications without departing from the spirit thereof. For example, the order of steps may be varied with the exception that there must be a delay of 1 to 2 hours after the carpet is shampooed and the room is vacuumed.

The invention claimed is:

1. A method of providing a room that is both clean and substantially free of allergens, wherein the room comprises at least hard and soft surfaces, bedding, carpet, and an HVAC system having coils, a filter, a condensation drip pan and at least one vent, the method comprising:
    placing an air purification system in the room;
    activating the air purification system;
    vacuuming all surfaces of the room with a vacuum cleaner;
    vacuuming the HVAC coils;
    applying a disinfectant to the HVAC coils;
    replacing HVAC filter;
    vacuuming at least one HVAC vent;
    applying the disinfectant to the at least one HVAC vent;
    placing an enzyme tablet in the HVAC condensation drip pan;
    applying the disinfectant to all hard surfaces in the room;
    applying the disinfectant to all soft surfaces in the room other than carpet;
    treating the carpet;
    treating room with hydroxyl treatment;
    vacuuming the carpet with the vacuum cleaner;
    encasing bedding in protectors;
    applying a protectant to soft surfaces with a fogger;
    applying a protectant to hard surfaces with a cloth;
    placing the air purification system for normal usage; and
    providing an upright vacuum in the room for occupant usage.

2. The method according to claim 1 wherein:
    the air purification system contains an ionization system, a carbon filter, a HEPA filter, and oxidizers to prevent contamination.

3. The method according to claim 1 wherein:
the vacuum cleaner contains a HEPA filter.

4. The method according to claim 1 wherein:
the enzyme tablet contains no tea tree oil.

5. The method according to claim 1 wherein:
the disinfectant contains no cleaning solutions.

6. The method according to claim 1 wherein:
the disinfectant is applied to the hard surfaces with a cloth.

7. The method according to claim 1 wherein:
the disinfectant is applied to soft surfaces with a microsprayer or ULV fogger.

8. The method according to claim 1 wherein treating the carpet comprises the following steps:
applying crystallizing shampoo to carpet;
applying dust mite and flea control product to carpet;
applying allergen and odor neutralizer to carpet; and
applying disinfectant to carpet.

9. The method according to claim 1 wherein:
the upright vacuum cleaner contains a HEPA filter.

10. A method of providing a room that is both clean and substantially free of allergens, wherein the room comprises at least hard and soft surfaces, carpet, and an HVAC system having coils, a filter, a condensation drip pan and at least one vent, the method comprising:
placing an air purification system in the room, the air purification system containing an ionization system, a carbon filter, a HEPA filter, and oxidizers to prevent contamination;
activating the air purifier system;
vacuuming all surfaces of the room with a vacuum cleaner, the vacuum cleaner including a HEPA filter;
vacuuming the HVAC coils;
applying a cleaning and disinfectant solution to the HVAC coils;
replacing HVAC filter;
vacuuming the at least one HVAC vent;
applying a disinfectant to the at least one HVAC vent, the disinfectant being free of cleaning solution;
placing an enzyme tablet in an HVAC condensation drip pan, the enzyme tablet being free of tea tree oil;
applying the disinfectant with a cloth to all hard surfaces in the room;
applying the disinfectant with a microsprayer or ULV fogger to all soft surfaces in the room other than carpet;
treating the carpet with the following steps:
applying crystallizing shampoo to carpet with a multi-function cleaning device;
applying dust mite and flea control product to carpet;
applying allergen and odor neutralizer to carpet; and
applying the disinfectant to carpet with a microsprayer or ULV fogger;
treating room with hydroxyl treatment;
vacuuming the carpet with the vacuum cleaner;
encasing bedding in protectors;
applying a protectant to soft surfaces with a ULV fogger;
applying a protectant to hard surfaces with a cloth;
placing air purification system for normal usage; and
providing an upright vacuum with a HEPA filter for occupant usage.

* * * * *